United States Patent
Sanders et al.

(10) Patent No.: US 10,912,651 B2
(45) Date of Patent: *Feb. 9, 2021

(54) SYSTEM AND METHOD FOR MODIFYING TALOCALCANEAL RELATIONSHIP IN A FOOT

(71) Applicant: Foot Innovations, LLC, Tampa, FL (US)

(72) Inventors: Roy W. Sanders, Tampa, FL (US); Sergio Gutierrez, Tampa, FL (US)

(73) Assignee: FOOT INNOVATIONS, LLC, Tampa, FL (US)

( * ) Notice: Subject to any disclaimer, the term of this patent is extended or adjusted under 35 U.S.C. 154(b) by 53 days.

This patent is subject to a terminal disclaimer.

(21) Appl. No.: 16/292,053

(22) Filed: Mar. 4, 2019

(65) Prior Publication Data

US 2019/0298538 A1 Oct. 3, 2019

Related U.S. Application Data

(63) Continuation of application No. 15/601,437, filed on May 22, 2017, now Pat. No. 10,219,909, which is a continuation of application No. 14/679,812, filed on Apr. 6, 2015, now Pat. No. 9,655,733, which is a continuation of application No. 12/732,509, filed on Mar. 26, 2010, now Pat. No. 9,005,301.

(60) Provisional application No. 61/173,959, filed on Apr. 29, 2009.

(51) Int. Cl.
*A61F 2/42* (2006.01)

(52) U.S. Cl.
CPC ............. *A61F 2/42* (2013.01); *A61F 2/4202* (2013.01); *A61F 2002/4207* (2013.01); *A61F 2002/4217* (2013.01); *A61F 2002/4223* (2013.01)

(58) Field of Classification Search
CPC .. A61F 2/42; A61F 2/4202; A61F 2002/4217; A61F 2002/4223
See application file for complete search history.

(56) References Cited

U.S. PATENT DOCUMENTS

| 4,450,591 A | 5/1984 | Rappaport | |
|---|---|---|---|
| 2007/0027547 A1* | 2/2007 | Rydell | A61F 2/4225 623/21.18 |
| 2007/0162016 A1* | 7/2007 | Matityahu | A61B 17/7059 606/281 |

OTHER PUBLICATIONS

U.S. Notice of Allowance on U.S. Appl. No. 15/601,437 dated Oct. 22, 2018.

(Continued)

*Primary Examiner* — Suba Ganesan
(74) *Attorney, Agent, or Firm* — Foley & Lardner LLP

(57) ABSTRACT

A system for modifying a talocalcaneal spatial relationship in a foot in a body, including a subtalar spacer having an articulating surface and implanted in the sinus tarsi of the foot and a fastener that fastens the subtalar spacer to a bone surface in the foot, in which the articulating surface of the subtalar spacer directs relative movement between the calcaneus and the talus of the foot.

20 Claims, 8 Drawing Sheets

(56) References Cited

OTHER PUBLICATIONS

U.S. Notice of Allowance on U.S. Appl. No. 14/042,485 dated Mar. 22, 2016.
U.S. Notice of Allowance on U.S. Appl. No. 14/042,485 dated Apr. 29, 2016.
U.S. Notice of Allowance on U.S. Appl. No. 14/679,812 dated Jan. 20, 2017.
U.S. Office Action on U.S. Appl. No. 14/679,812 dated Jun. 6, 2016.
U.S. Office Action on U.S. Appl. No. 15/601,437 dated May 18, 2018.

* cited by examiner

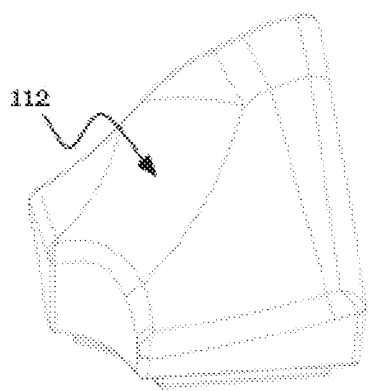
FIGURE 1A
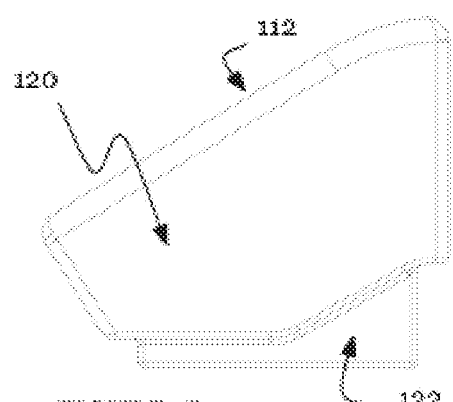
FIGURE 1B
FIGURE 1C
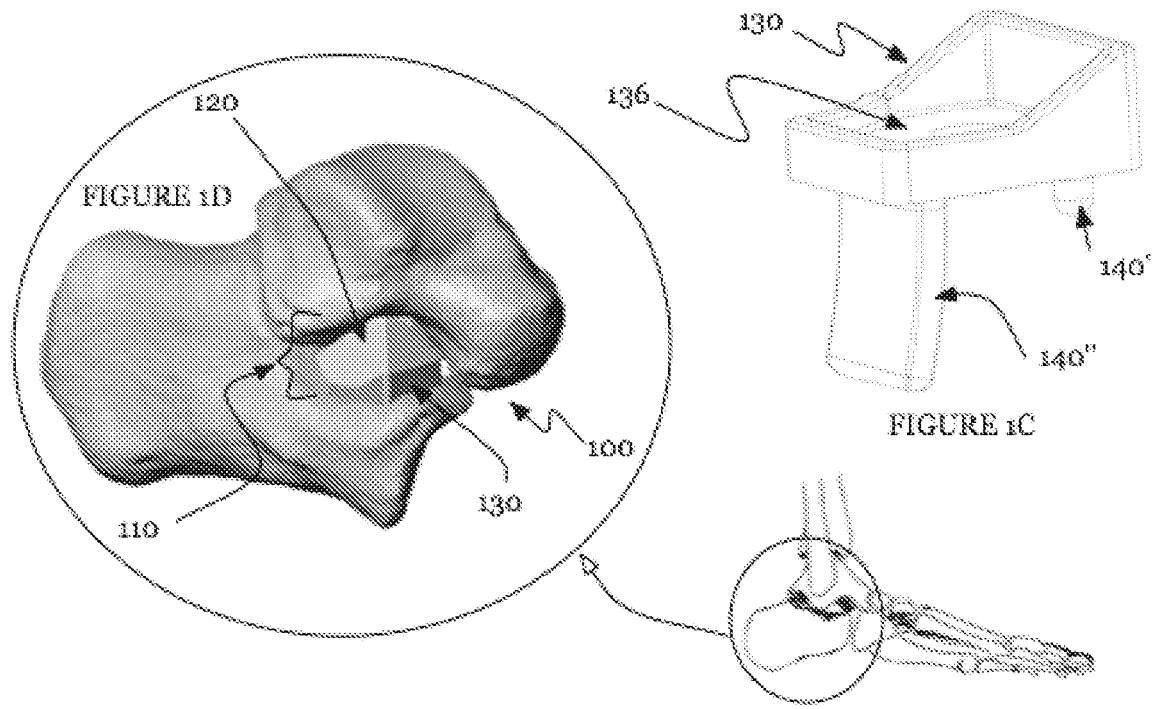
FIGURE 1D

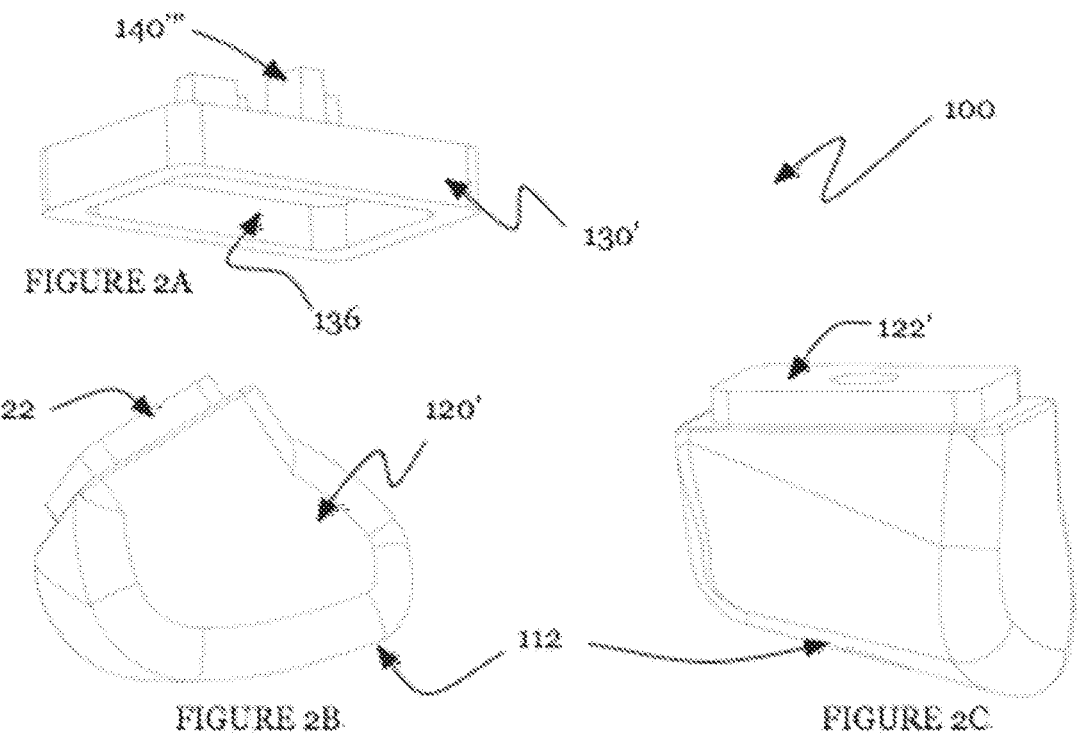
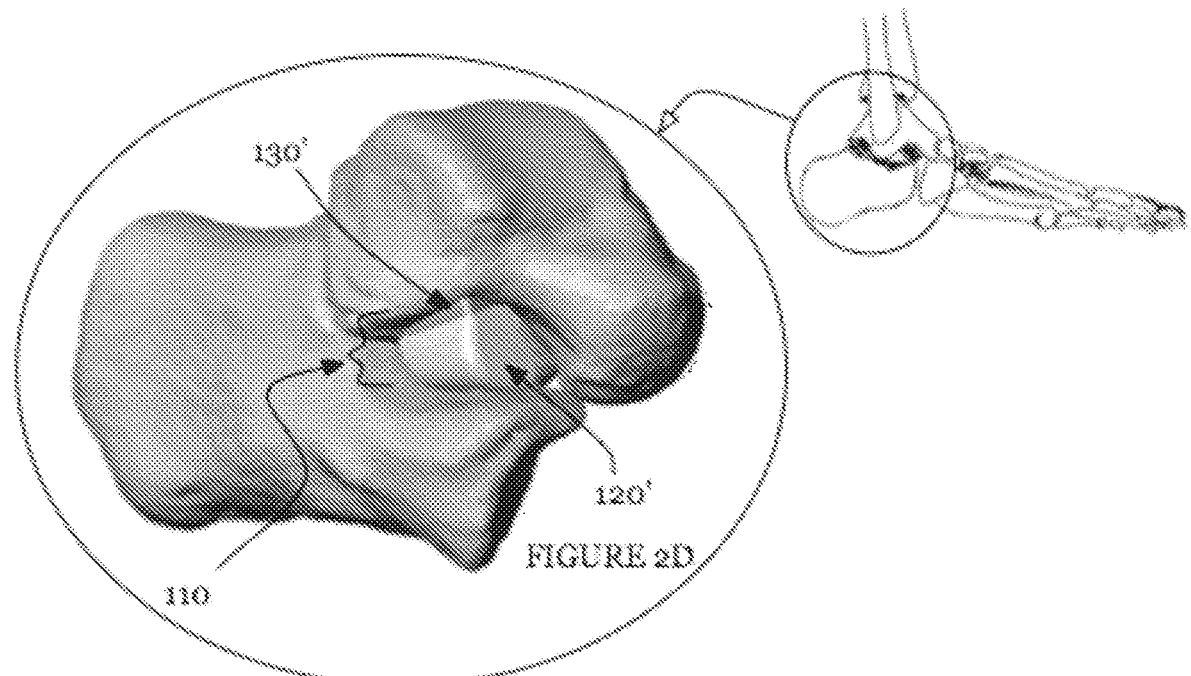

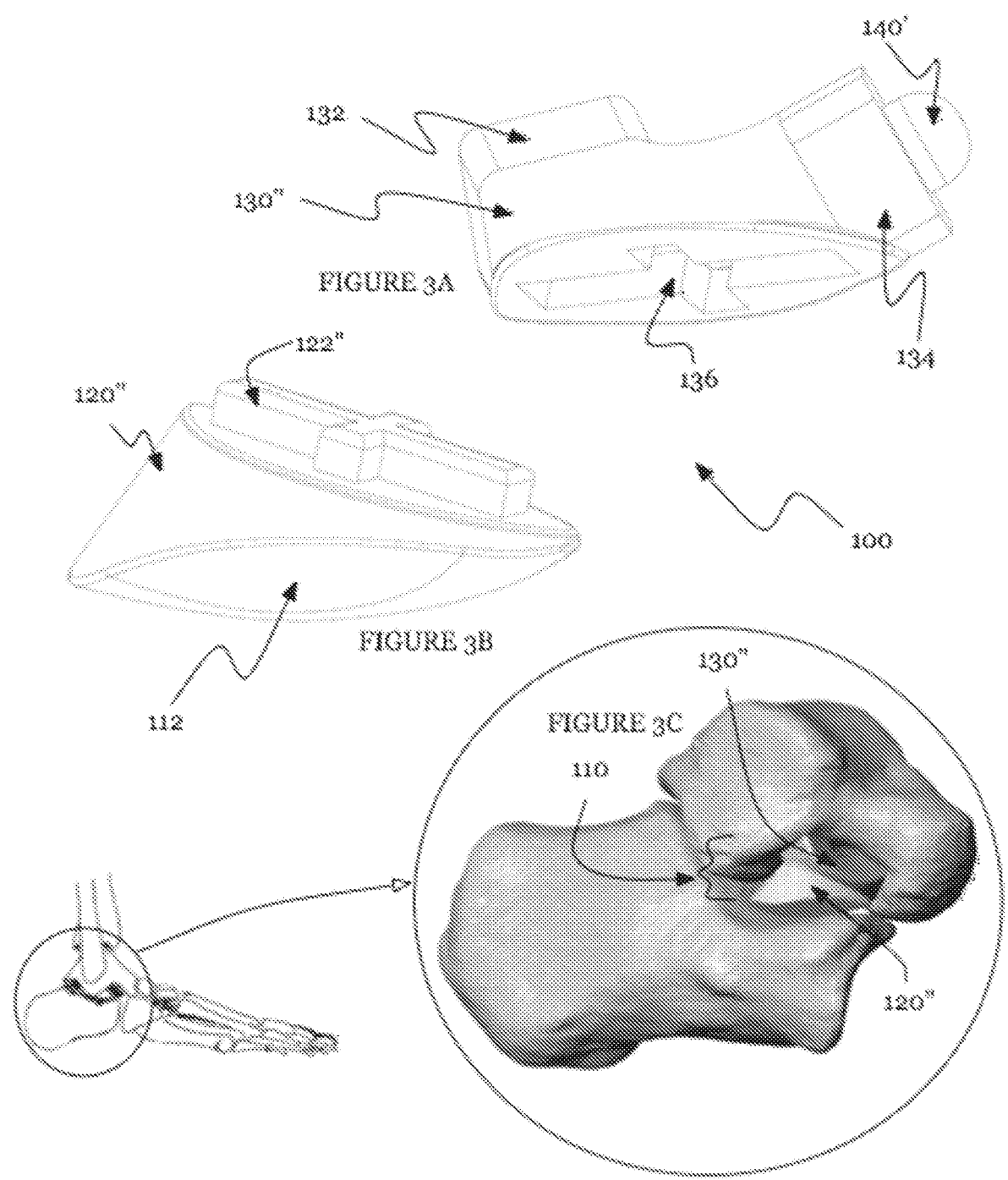

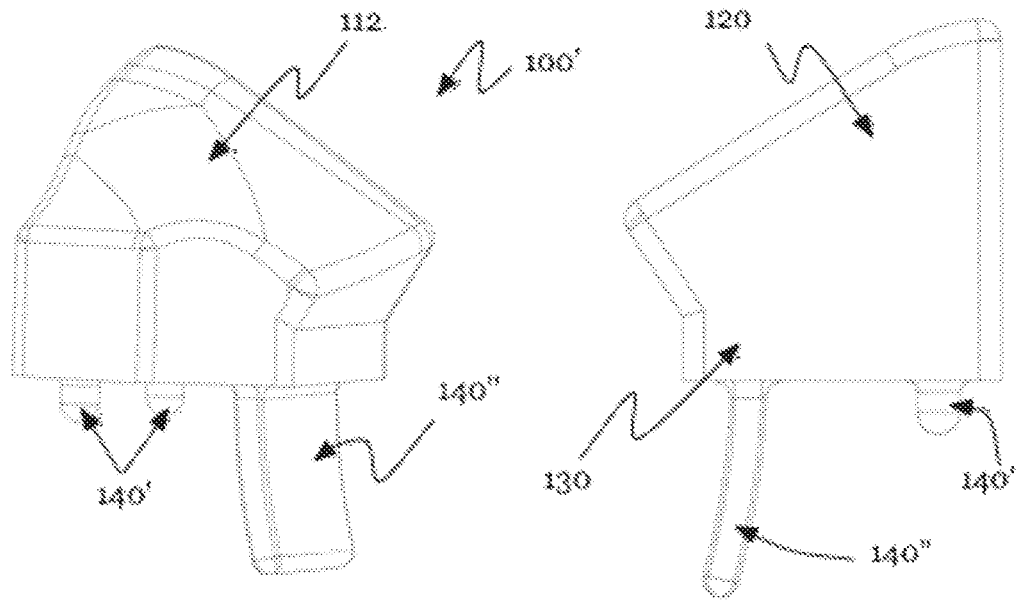
FIGURE 4A
FIGURE 4B
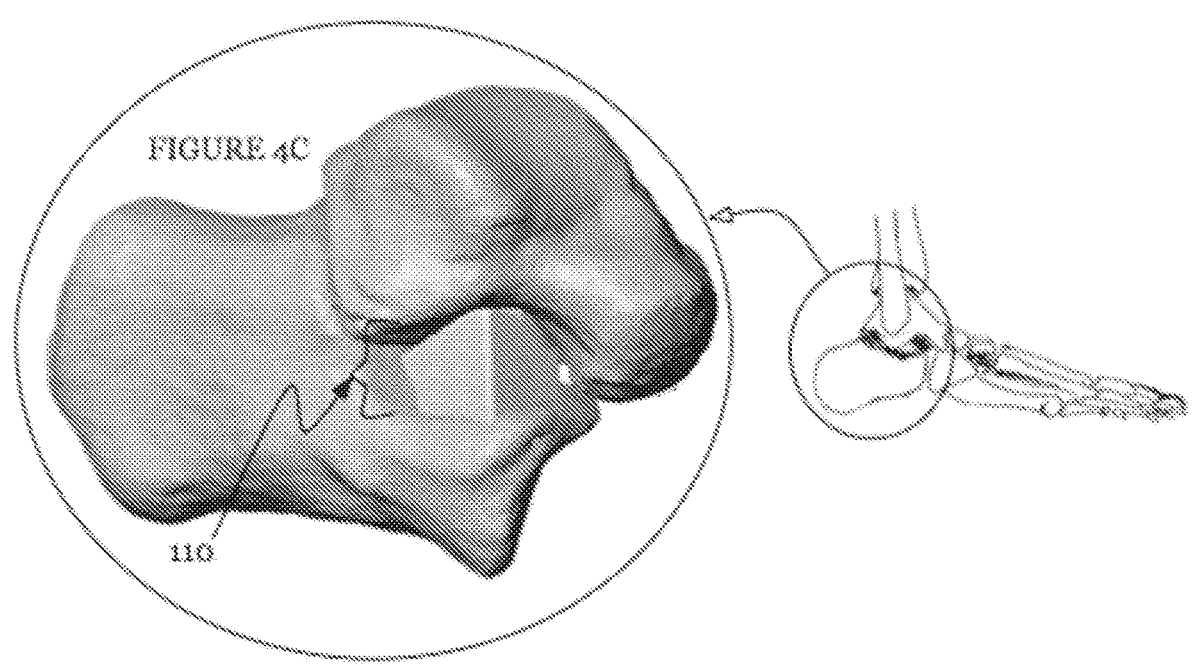
FIGURE 4C

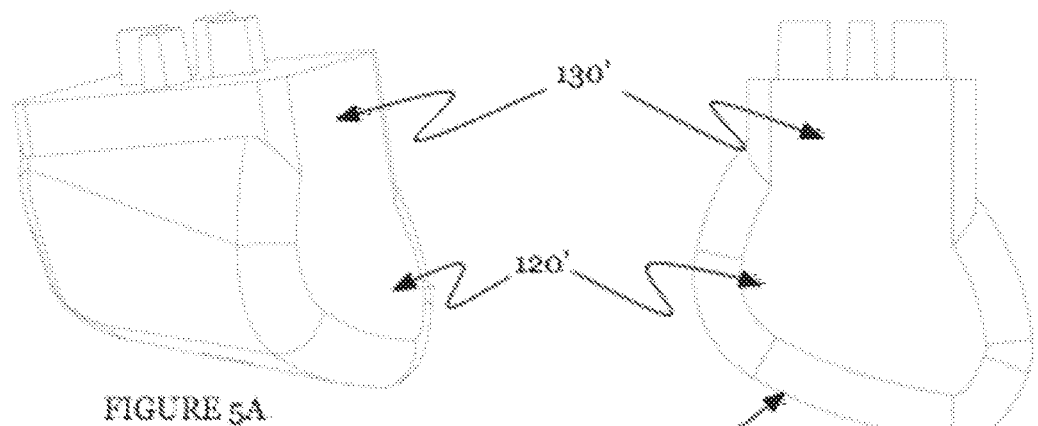
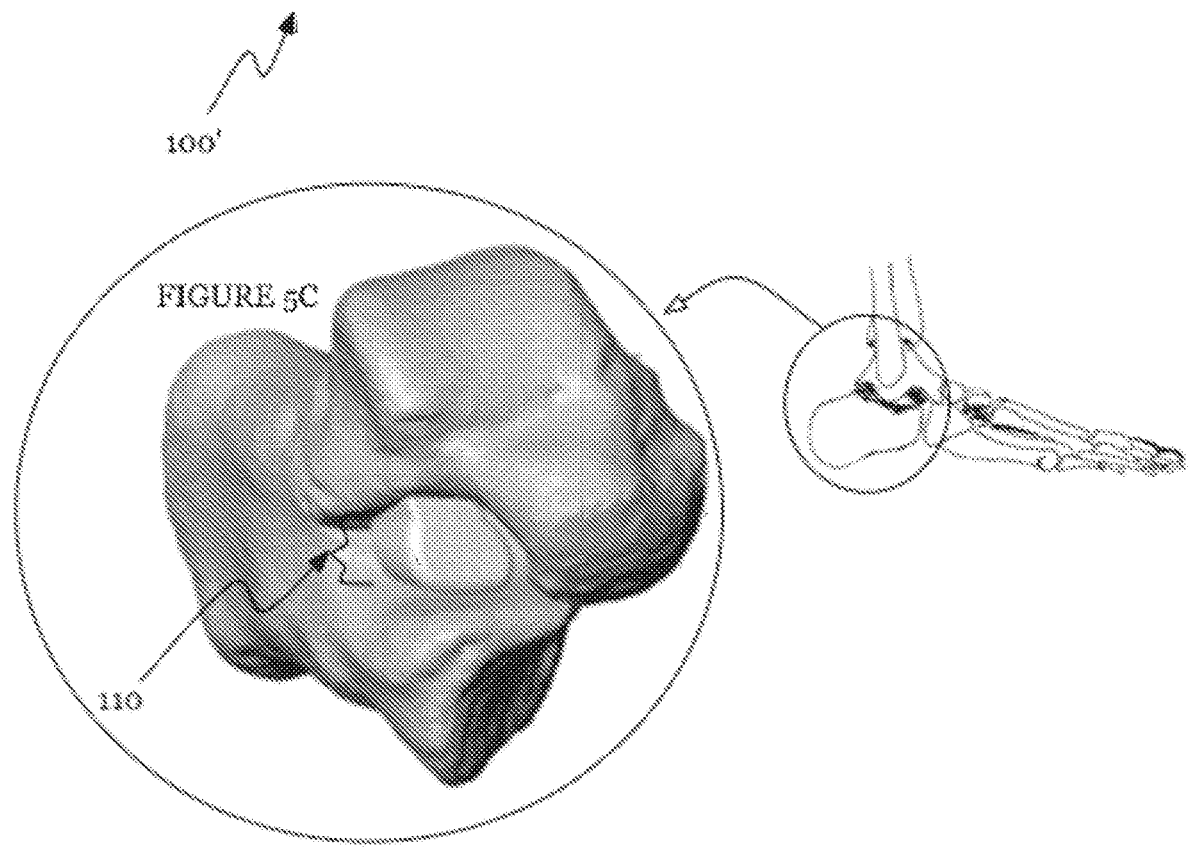

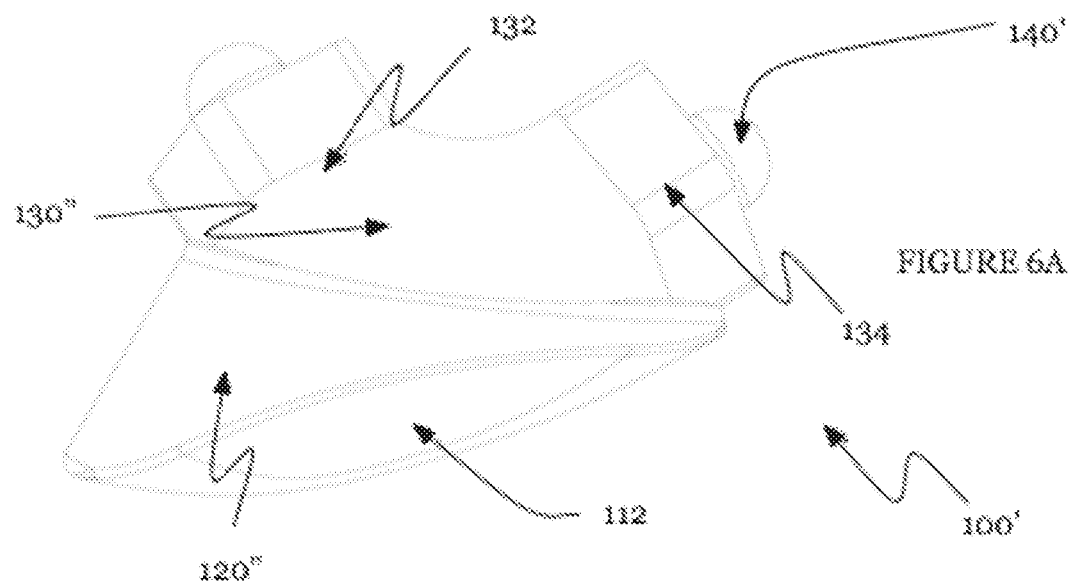
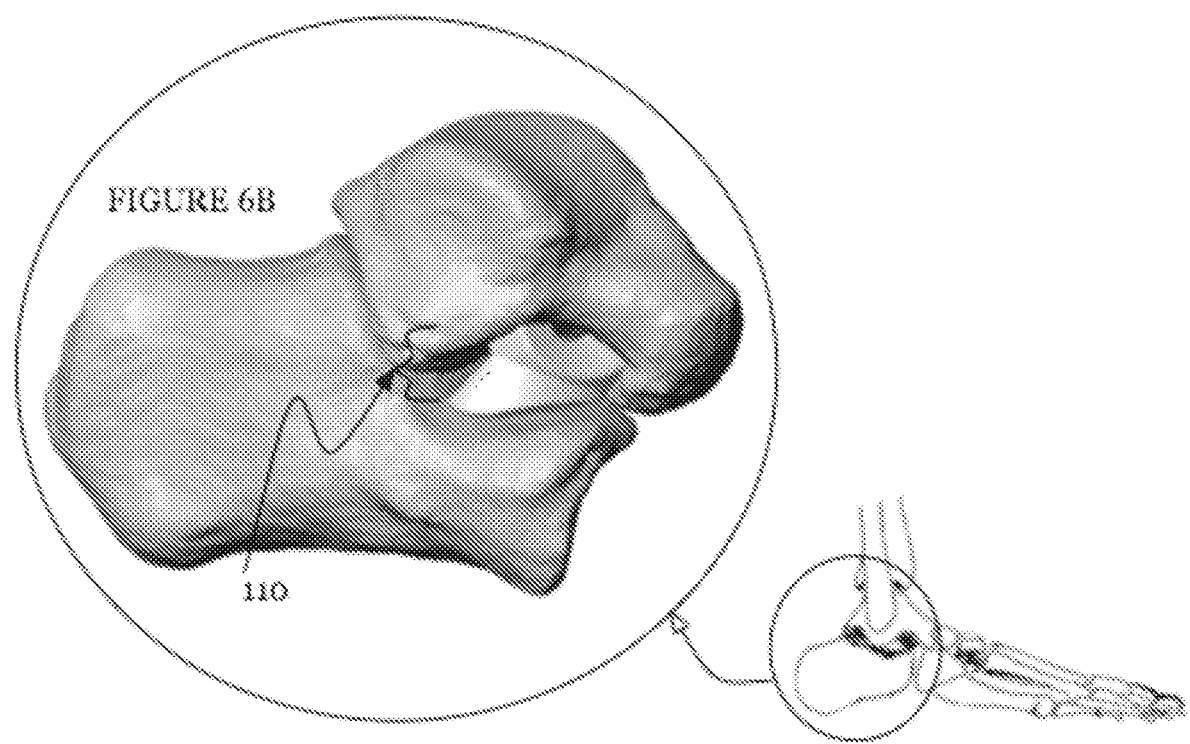

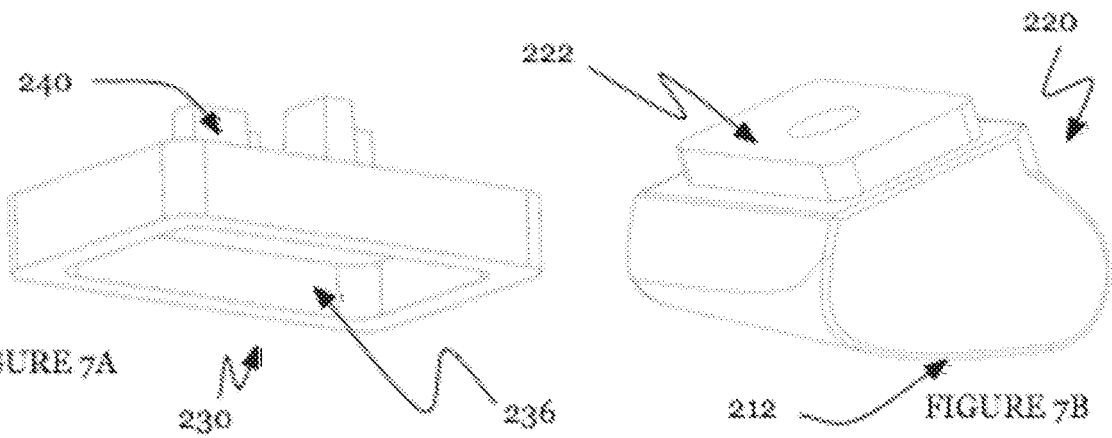
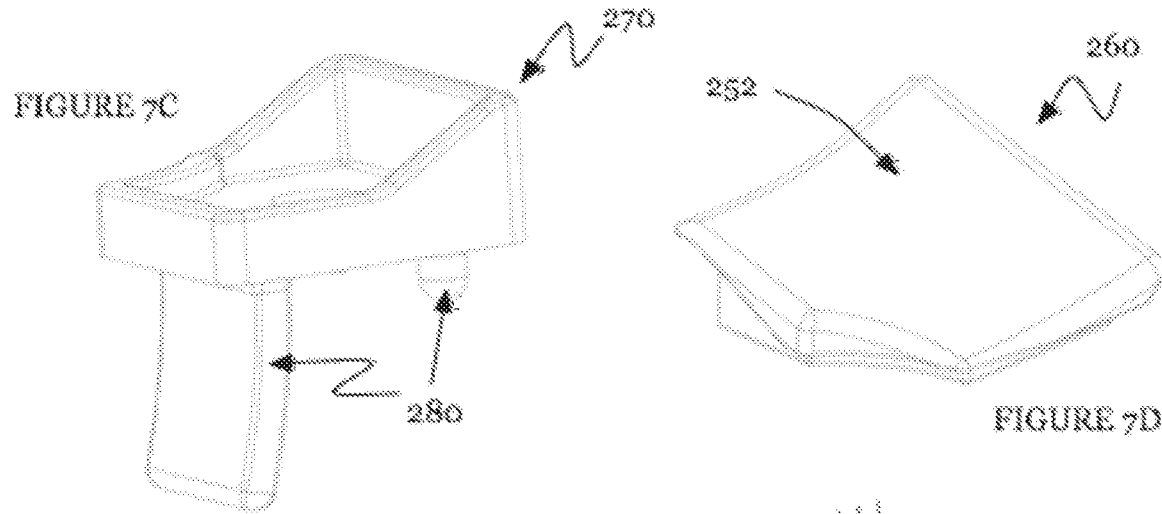
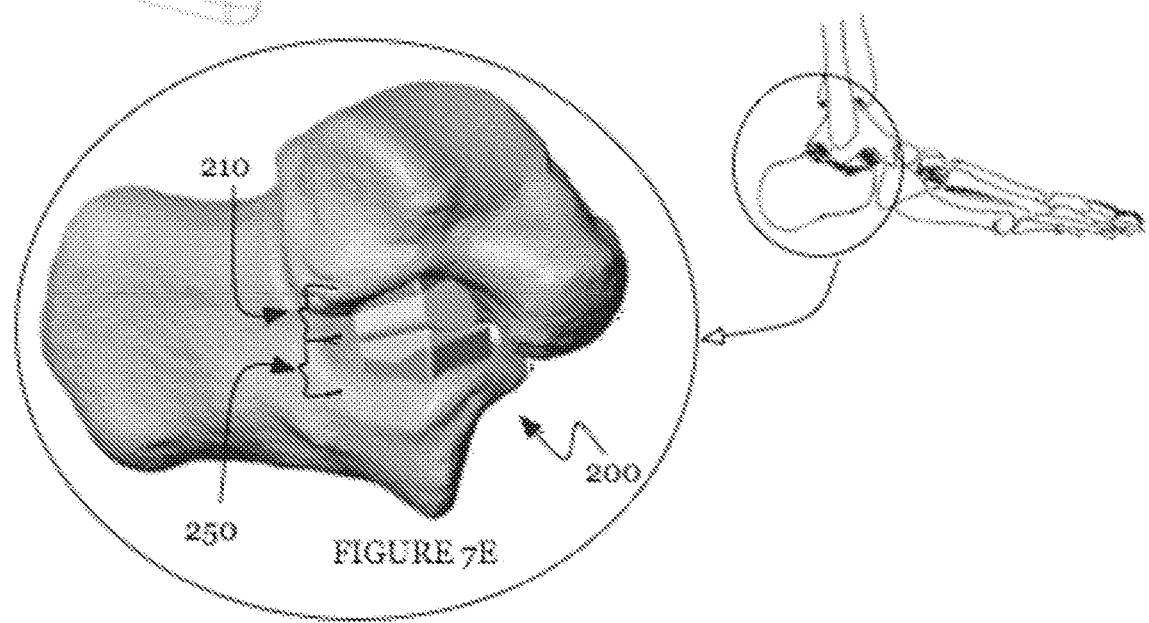

SYSTEM AND METHOD FOR MODIFYING TALOCALCANEAL RELATIONSHIP IN A FOOT

CROSS-REFERENCE TO RELATED APPLICATIONS

This application claims the benefit of U.S. Provisional Application No. 61/173,959, filed 29 Apr. 2009, which is incorporated in its entirety by this reference.

TECHNICAL FIELD

This invention relates generally to the implant field, and more specifically to an improved subtalar implant in the arthroereisis field.

BACKGROUND

Hyperpronation and flat feet ("fallen arches") are relatively common conditions of the feet that cause pain, such as during sports or daily activities like walking. These conditions can be caused by collapse thru the sinus tarsi. The sinus tarsi is a space between the talus and the calcaneus. It is funnel shaped with the larger opening on the lateral side of the foot progressing across the foot to end in a small medial opening between the two aforementioned bones. This lateral opening or space between the bones is normally maintained by the tension of ligaments located on the medial side of the talus and the posterior side of the calcaneus. When these ligaments fail due to either injury or disease, the talus is allowed to sublux or deviate from its normal position atop the calcaneus. This subluxation shifts the location of the calcaneus laterally (causing flatfoot), and allows the arch of the foot to collapse, increasing pronation. When this happens, the funnel shaped lateral opening of the sinus tarsi disappears.

Common noninvasive treatments for hyperpronation and flat feet include the use of foot orthotics and shoe modifications. Situations in which these treatments fail to relieve symptoms may require implantation of a subtalar arthroereisis, a type of "bone block", in the sinus tarsi to "reopen" the collapsed sinus tarsi. The subtalar arthroereisis typically acts as a spacer to limit motion of the talus. However, after implantation of current subtalar arthroereisis systems, the arthroereisis often become loose within the sinus tarsi, causing painful irritation of the surrounding tissue. Furthermore, these systems are not stable enough to accurately reconstitute the anatomy of the sinus tarsi. Once the system fails, removal is mandatory, with resultant painful collapse and the need for a formal subtalar arthrodesis (joint fusion).

Thus, there is a need in the implant field to create an improved subtalar arthroereisis. This invention provides such an improved subtalar arthroreisis.

BRIEF DESCRIPTION OF THE FIGURES

FIGS. 1A and 1B are a perspective view and a side view, respectively, of a first variation of the spacer body portion of the subtalar spacer of the first preferred embodiment of the system;

FIG. 1C is a perspective view of a first variation of the spacer mount portion and the fastener of the first preferred embodiment of the system;

FIG. 1D is an anterior-lateral view of a variation of the first preferred embodiment of the system assembled and implanted in the sinus tarsi;

FIG. 2A is a perspective view of a second variation of the spacer mount portion and the fastener of the first preferred embodiment of the system;

FIGS. 2B and 2C are perspective views of a second variation of the spacer body portion of the subtalar spacer of the first preferred embodiment of the system;

FIG. 2D is an anterior-lateral view of a variation of the first preferred embodiment of the system assembled and implanted in the sinus tarsi;

FIGS. 3A and 3B are perspective views of another version of the second variations of the spacer mount portion and the spacer body portion, respectively, of the subtalar spacer of the first preferred embodiment of the system;

FIG. 3C is an anterior-lateral view of a variation of the first preferred embodiment of the system assembled and implanted in the sinus tarsi;

FIGS. 4A and 4B are perspective and side views, respectively, of the subtalar spacer and fastener of an alternative embodiment of the system;

FIG. 4C is an anterior-lateral view of an alternative embodiment of the system implanted in the sinus tarsi;

FIGS. 5A and 5B are perspective and side views, respectively, of the subtalar spacer and fastener of an alternative embodiment of the system;

FIG. 5C is an anterior-lateral view of an alternative embodiment of the system implanted in the sinus tarsi;

FIG. 6A is a side view of the subtalar spacer and fastener of the an alternative embodiment of the system;

FIG. 6B is an anterior-lateral view of an alternative embodiment of the system implanted in the sinus tarsi;

FIGS. 7A through 7D are perspective views of a first spacer mount portion, first spacer body portion, second spacer mount portion, and second body portion, respectively, of an exemplary second preferred embodiment of the system;

FIG. 7E is an anterior-lateral view of the first and second subtalar spacers of an exemplary second preferred embodiment of the system implanted in the sinus tarsi.

DESCRIPTION OF THE PREFERRED EMBODIMENTS

Figure 8:
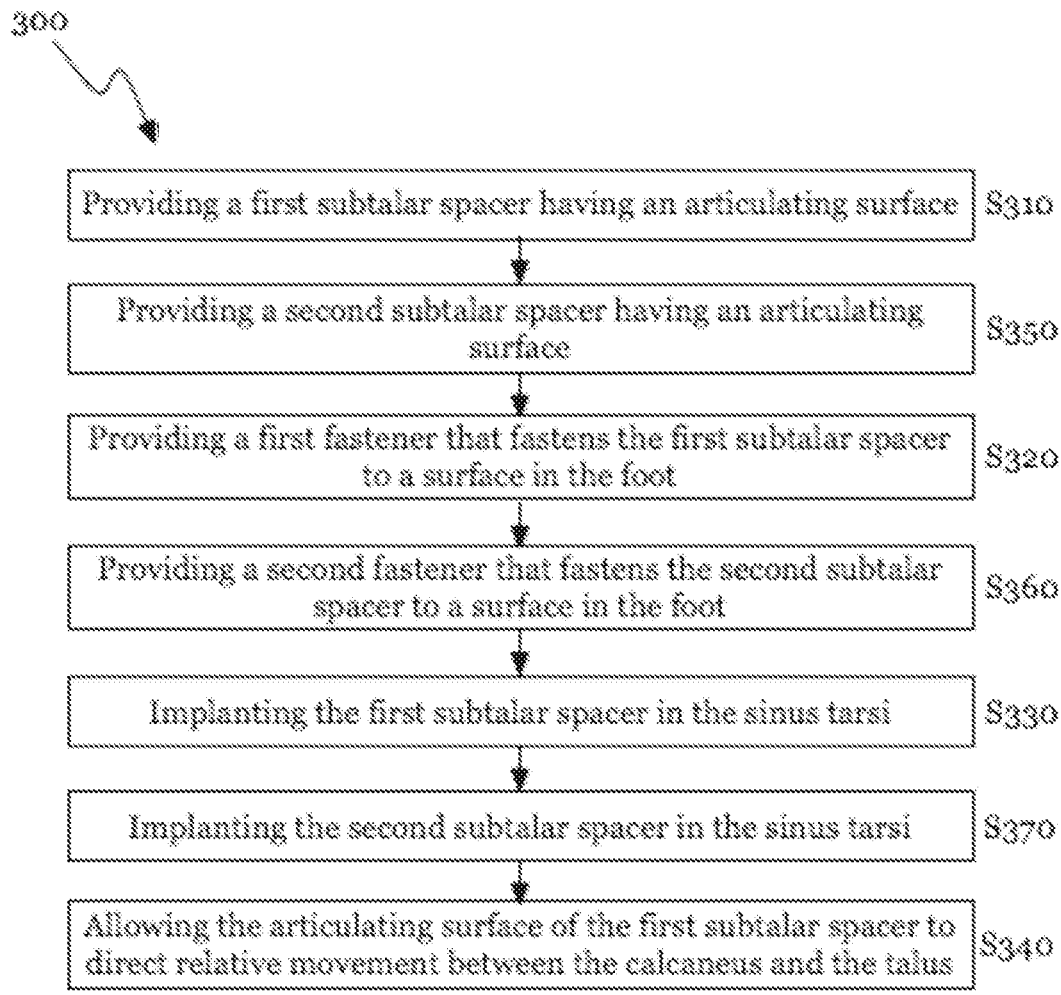
FIG. 8 is a schematic of an embodiment of the method for modifying talocalcaneal relationship in a foot.

The following description of preferred embodiments of the invention is not intended to limit the invention to these preferred embodiments, but rather to enable any person skilled in the art to make and use this invention.

As shown in FIGS. 1 through 7, the system 100 for modifying a talocalcaneal spatial relationship of the preferred embodiment includes a subtalar spacer 110 having an articulating surface 112, and a fastener 140 that fixes the subtalar spacer 110 to a bone surface in the foot, in which the articulating surface 112 of the subtalar spacer 110 directs relative movement between the calcaneus and the talus of the foot. The system 100 preferably restores a normal talocalcaneal spatial relationship by restoring the sinus tarsi in the foot and directing the compressive and sliding forces generated between the talus and calcaneus as the talus moves over the calcaneus during daily activities. The sliding motion creates a movable yet stable joint for reducing conditions caused by a collapsed sinus tarsi, including hyperpronation of the foot and flat feet.

The subtalar spacer 110 of the system 100 functions to restore the sinus tarsi space in a foot of a body. The subtalar spacer 110 is preferably implanted in the sinus tarsi of the foot and elevates (when the body is in a standing position)

the talus bone relative to the calcaneus bone of the foot. The subtalar spacer 110 preferably includes an articulating surface 112, a spacer body portion 120, and a spacer mount portion 130.

The articulating surface 112 of the subtalar spacer 110 is preferably a surface on the spacer body portion 120 or any suitable portion of the subtalar spacer 110 that functions to direct forces between the talus and calcaneus as the talus moves over the calcaneus during daily activities. The articulating surface 112 preferably provides a surface for a bone, another spacer body portion, and/or any suitable tissue or surface to contact the subtalar spacer 110. As shown in FIGS. 1 through 7, the articulating surface 112 is preferably generally smooth to facilitate a sliding motion on the articulating surface 112, but may be ribbed, grooved, and/or have any suitable texture for articulating with another surface in any suitable articulating motion such a rolling and/or rubbing.

The spacer body portion 120 of the subtalar spacer 110 functions to provide structural support for the restoration of the sinus tarsi. The spacer body portion 120 may be one of several variations. In a first variation, as shown in FIGS. 1A through 1D, the spacer body portion 120 is adapted to be fixed to the calcaneus bone. As shown in FIGS. 1A and 1B, the spacer body portion 120 is preferably shaped to fill a significant portion of the sinus tarsi, and the articulating surface 112 is preferably contoured to articulate with an inferior surface of the talus bone. In particular, as shown in FIG. 1E, the articulating surface 112 is preferably on the superior side of the spacer body portion 120 and is gently sloped to articulate in a sliding motion with the anterior and/or lateral aspects of the inferior surface of the talus bone, but the articulating surface 112 may alternatively articulate with any suitable surface in any suitable motion. In a second variation, as shown in FIGS. 2A through 2D, the spacer body portion 120' is adapted to be fixed to the talus bone. As shown in FIGS. 2B and 2C, the spacer body portion is preferably shaped to fill a significant portion of the sinus tarsi, and the articulating surface 112 is preferably contoured to articulate with a superior surface of the calcaneus bone. In particular, as shown in FIG. 2D, the articulating surface 112 is preferably on the inferior side of the spacer body portion 120' and is sloped and contoured in a convex manner to articulate with a portion of the superior surface of the calcaneus bone in a sliding motion. Alternatively, as shown in FIGS. 3B and 3C, the articulating surface 112 on the spacer body portion 120" may be sloped and contoured in a concave manner to complement another portion of the superior surface of the calcaneus bone. However, the articulating surface 112 may articulate with any suitable surface in any suitable motion.

The spacer mount portion 130 of the subtalar spacer 110 functions to provide a surface for the fastener 140 to fasten the subtalar spacer 110 to a surface. By fastening the subtalar spacer 110 to a surface, the spacer mount portion 130 fixes the subtalar spacer 110 within the sinus tarsi, helping to promote bony ingrowth into the implant that reduces the likelihood of the subtalar spacer 110 loosening within the sinus tarsi and reduces pain. The spacer mount portion 130 may be one of several variations. In a first variation, as shown in FIGURES IC and ID, the spacer mount portion 130 is adapted to attach to the calcaneus bone. The inferior side of the spacer mount portion 130 preferably includes a generally flat planar surface for the fastener 140, which increases stability of the subtalar spacer 110 on the bone and simplifies surgical preparation for the implantation of the subtalar spacer 110. However, the inferior side of the spacer mount portion 130 may alternatively be curved, sloped, complementary to the natural contours of the calcaneus, a custom surgically prepared surface, or any suitable geometry. In a second variation, as shown in FIGS. 2A and 2D, the spacer mount portion is adapted to attach to the talus bone. The superior side of the spacer mount portion 130' is preferably similar to the inferior side of the spacer mount of the first variation, except that the superior side of the spacer mount portion of the second variation may be curved, sloped, complementary to the natural contours of the talus, or any suitable geometry. As shown in FIGS. 3A and 3C, the spacer mount portion 130" of the second variation may alternatively include a branch that has a first end 132 and a second end 134 that are adapted to attach to the talus bone. As shown in FIG. 3C, the multiple ends of the branch preferably provide additional mounting areas to improve fixation of the subtalar spacer 110 to the surface, and facilitate proper positioning of the alternative spacer body portion of the second variation to articulate with the calcaneus bone. The first end 132 is preferably a lateral end that is adapted to attach to a lateral portion of the inferior side of the talus, and the second end 134 is preferably a medial end that is adapted to attach to a medial portion of the anterior/inferior side of the talus. However, the first and second ends of the branch may alternatively be adapted to attach to any suitable portions of the talus and/or any suitable surface. Alternatively, the branch may include more than two ends, each of which is adapted to attach to a suitable individual portion of the talus or any other suitable surface.

The spacer body portion 120 and the spacer mount portion 130 are preferably separate components and the spacer body portion 120 is preferably coupled to the spacer mount portion 130. As shown in FIGS. 1 through 3, the spacer body portion 120 preferably includes a boss 122 and the spacer mount portion 130 preferably includes a recess 136, such that the boss 122 of the spacer body portion 120 couples to the recess 136 of the spacer mount portion 130. The boss of the spacer body portion 120 may have footprint of a square shape 122 as shown in FIG. 1B, a rectangular shape 122' as shown in FIG. 2C, a cross shape 122" as shown in FIG. 3B, circular, any suitable polygon, and/or any suitable shape. Alternatively, the spacer body portion may include a plurality of bosses. The spacer body portion 120 may include a key and the spacer mount portion 130 may include a keyway such that the spacer body portion and the spacer mount portion are restrained to couple in one orientation to help prevent accidental reversal or undesired orientations of the spacer body portion relative to the spacer mount portion. The spacer body portion 120 preferably couples to the spacer mount portion 130 in a permanent fashion, but may alternatively be semi-permanent and/or selectively removable to facilitate applications such as adapting to a growing and changing skeletal frame such as in a child, and obtaining a trial-and-error custom fit. The spacer body portion 120 preferably couples to the spacer mount portion 130 with a press-fit, but may alternatively and/or additionally couple to the spacer mount portion with cement, screws, bolts, and/or any suitable adhesive or fastener.

The spacer body portion 120 is preferably made of a durable, shock-absorbent and biocompatible material such as ultra high molecular weight polyethylene, but may alternatively and/or additionally be made of any suitable material. The spacer body portion is preferably made in an injection molding process, but may alternatively be made by milling, 3D printing, or any suitable manufacturing process. The spacer mount portion 130 is preferably made of a durable, biocompatible material such as titanium, but may alternatively and/or additionally be made of any suitable material. The spacer mount portion is preferably made in a casting or molding process, but may alternatively be made by milling or any suitable manufacturing process.

The subtalar spacer 110 may alternatively include multiple spacer body portions 120. As an example, the subtalar spacer 110 may include multiple spacer body portions 120 that couple to each other and/or to the spacer mount portion, in a puzzle-like fashion, and/or in a manner similar to that described above. Multiple spacer body portions 120 may be useful for some situations, such as swapping individual spacer body portions to obtain a custom fit.

In other alternatives, as shown in FIGS. 4 through 6, the spacer body portion 120 and the spacer mount portion 130 may alternatively be integrated into a single component. In these alternatives, the geometries of the spacer body portions and spacer mount portions are similar to those described above and shown in FIGS. 1 through 3. In particular, the subtalar spacer with integrated spacer body portion 120 and spacer mount portion 130 may be designed to be fixed to the calcaneus (FIG. 4), or to the talus (FIGS. 5 and 6).

The fastener 140 of the system 100 functions to fasten the subtalar spacer 110 to a bone surface in the foot. In particular, the fastener 140 preferably fastens the subtalar spacer 110 to the calcaneus bone or the talus bone. The fastener 140 may, however, fasten the subtalar spacer 110 to any suitable surface. The fastener 140 is preferably integrated into the spacer mount portion of the subtalar spacer 110, but may alternatively be a separate component and coupled to the spacer mount portion 130. The fastener 140 preferably fastens the subtalar spacer 110 to a bone surface by being inserted into the bone and promoting bony ingrowth into the system. The fastener 140 is preferably a protrusion in the shape of a peg 140' (as shown in FIGS. 1C and 3A), a tab 140" (as shown in FIG. 1C), a keel 140'" (as shown in FIG. 2A), and/or any suitable shape. However, the fastener 140 may alternatively and/or additionally include bone cement, screws, bolts, and/or any suitable adhesive or fastener. As shown in FIGURES IC, 2A, and 3A, the fastener preferably includes a plurality of these structures, to anchor the subtalar spacer 110 to the bone. The fastener 140 may further include threads, bumps, notches, and/or any suitable texture to encourage bone growth for tissue fixation of the fastener within the bone, and may alternatively and/or additionally include bone growth factors to enhance bone growth. The fastener 140 is preferably inserted into the bone after the bone is surgically prepared, such as by leveling and/or drilling holes into the bone.

The fastener 140 is preferably made of a biocompatible material and through a manufacturing process similar to that of the spacer mount portion 130 of the subtalar spacer 110.

In a second preferred embodiment, as shown in FIGS. 7A through 7E, the system 200 includes a first subtalar spacer 210, a first fastener 240, a second subtalar spacer 250 and a second fastener 280. The first fastener 240 and second fastener 280 are preferably identical to the fastener 140 of the first preferred embodiment of the system 100. The first subtalar spacer 210 (which includes a first spacer body portion 220 and a first spacer mount portion 230) and second subtalar spacer 250 (which includes a second spacer body portion 260 and a second spacer mount portion 280) are preferably similar to the subtalar spacer 110 of the first preferred embodiment of the system 100, except as described below. As shown in FIG. 7E, the second subtalar spacer 250 is preferably adapted to be implanted in the sinus tarsi directly opposite the first subtalar spacer 210. The spacer body portions 220 and 260 of the first and second subtalar spacers, respectively, preferably are generally complementary and fill a significant portion of the sinus tarsi when implanted. The articulating surface 212 of the first subtalar spacer 210 preferably articulates with the articulating surface 252 of the second subtalar spacer 250. In the embodiment as shown in FIG. 7E, the articulating surfaces of the first and second subtalar spacers are preferably complementary to each other, such that the articulating surfaces 212 and 252 of the first and second subtalar spacers, respectively, articulate with each other in a sliding motion. However, the articulating surfaces of the first and second subtalar spacers may alternatively articulate with each other in a rolling, rubbing, or any suitable articulating motion. For example, as shown in FIG. 7E, a first subtalar spacer 210 may be implanted in the talus bone and a second subtalar spacer 250 may be implanted in the calcaneus bone, such that the articulating surface 212 of the first subtalar spacer 210 contacts the articulating surface 252 of the second subtalar spacer in a sliding manner. In this example, the articulating surfaces of the first and second subtalar spacers are made of ultra high molecular weight polyethylene for polyethylene-polyethylene articulating contact, which reduces the tendency of painful loosening of the first and second subtalar spacers. However, the articulating surfaces of the first and second subtalar spacers may alternatively be made of any suitable material, and be contoured in any suitable manner for articulation with each other.

As shown in FIG. 8, a method 300 for modifying a talocalcaneal spatial relationship in a foot in a body includes the steps of providing a first subtalar spacer having an articulating surface S310, providing a first fastener that fastens the subtalar spacer to a surface in the foot S320, implanting the first subtalar spacer in the sinus tarsi of the foot S330, and allowing the articulating surface of the first subtalar spacer to direct relative movement between the calcaneus and the talus of the foot S340. The method preferably restores a normal talocalcaneal spatial relationship by restoring the sinus tarsi in the foot, thereby reducing conditions caused by a collapsed sinus tarsi, including hyperpronation and flat feet.

The step of implanting the first subtalar spacer in the sinus tarsi of the foot S330 preferably includes preparing a surface and inserting the fastener into the bone surface. The surface is preferably on the calcaneus bone or the talus bone, but may alternatively be any suitable bone or any suitable surface. Preparing the surface is preferably similar to typical conventional preparation for surgical implantations and may include drilling, sanding, and/or other manipulations of the bone that are known to one ordinarily skilled in the art. Inserting the fastener into the bone surface preferably includes inserting a peg, tab, keel, or any suitable portion of the fastener into the bone surface. Alternatively, the step of implanting the first subtalar spacer in the sinus tarsi of the foot may include applying cement, or utilizing screws, bolts, and/or any suitable adhesive or fastener.

In one variation of the method, the step of allowing the articulating surface of the first subtalar spacer to direct relative movement between the calcaneus and the talus of the foot S340 preferably includes the step of allowing the articulating surface of the first subtalar spacer to articulate with a surface of the calcaneus. The articulation between the first subtalar spacer and the calcaneus is preferably a sliding motion, but may additionally and/or alternatively be a rolling, rubbing, and/or any suitable articulation. The sliding motion preferably helps direct forces between the talus and calcaneus as the talus moves over the calcaneus during daily activities, creating a movable yet stable joint. In this variation, the step of providing a fastener that fastens preferably includes providing a fastener that fastens the first subtalar spacer to the talus.

In another variation of the method, the step of allowing the articulating surface of the first subtalar spacer to direct relative movement between the calcaneus and the talus of the foot S340 preferably includes the step of allowing the articulating surface of the first subtalar spacer to articulate with a surface of the talus. The articulation between the first subtalar spacer and the calcaneus is preferably a sliding motion, but may additionally and/or alternatively be a rolling, rubbing, and/or any suitable articulation. The sliding motion preferably helps direct forces between the talus and calcaneus as the talus moves over the calcaneus during daily activities, creating a movable yet stable joint. In this variation, the step of providing a fastener that fastens preferably includes providing a fastener that fastens the first subtalar spacer to the calcaneus.

In another embodiment of the method, the method 300 preferably further includes the steps of providing a second subtalar spacer having an articulating surface S350, providing a second fastener that fastens the second subtalar spacer to a surface in the foot S360, and implanting the second subtalar spacer in the sinus tarsi of the foot S370. In this embodiment, the step of allowing the articulating surface of the first subtalar spacer to direct relative movement between the calcaneus and the talus of the foot S340 preferably includes allowing the articulating surface of the first subtalar spacer to articulate with the articulating surface of the second subtalar spacer.

As a person skilled in the art will recognize from the previous detailed description and from the figures and claims, modifications and changes can be made to the preferred embodiments of the invention without departing from the scope of this invention defined in the following claims.

We claim:

1. An apparatus for modifying a talocalcaneal spatial relationship in a foot, comprising:
   a subtalar spacer configured to be implanted in the sinus tarsi of the foot, the subtalar spacer including:
      a spacer body portion including an articulating surface, the spacer body portion shaped to fit within and fill a majority portion of the sinus tarsi so as to elevate the talus bone relative to the calcaneus bone, the articulating surface contoured to articulate with one of an inferior surface of the talus bone or a superior surface of the calcaneus bone; and
      a spacer mount portion including a fastener extending from the spacer mount portion, the fastener configured to fasten the subtalar spacer to the other of the inferior surface of the talus bone or the superior surface of the calcaneus bone.

2. The apparatus of claim 1, wherein the articulating surface is smooth.

3. The apparatus of claim 1, wherein the articulating surface is at least one of ribbed or grooved.

4. The apparatus of claim 1, wherein the fastener extends from a superior side of the spacer mount portion, the superior side having a geometry that is at least one of curved, sloped, or complementary to natural contours of the talus bone.

5. The apparatus of claim 1, wherein the spacer mount portion includes a branch having a first end and a second end that are both configured to attach to the other of the inferior surface of the talus bone or the superior surface of the calcaneus bone.

6. The apparatus of claim 1, wherein the spacer body portion is configured to be removably coupled to the spacer mount portion.

7. The apparatus of claim 6, wherein the spacer body portion includes a boss and the spacer mount portion includes a recess such that the boss of the spacer body portion is configured to couple to the recess of the spacer mount portion.

8. The apparatus of claim 1, wherein the spacer body portion is made of a biocompatible material.

9. The apparatus of claim 1, wherein the fastener is removably coupled to the spacer mount portion.

10. The apparatus of claim 1, wherein the fastener is configured to promote bony ingrowth into the apparatus.

11. The apparatus of claim 1, wherein the spacer body portion is integral to the spacer mount portion.

12. The apparatus of claim 1, wherein the fastener includes at least one of a peg, a tab, or a keel.

13. The apparatus of claim 1, wherein the spacer mount portion is configured to attach to the calcaneus bone and an inferior side of the spacer mount portion includes a flat planar surface of the fastener.

14. The apparatus of claim 1, wherein the spacer mount portion is at least one of curved, sloped, or complementary to natural contours of the calcaneus bone.

15. An apparatus for modifying a talocalcaneal spatial relationship in a foot, comprising:
   a first subtalar spacer configured to be implanted in the sinus tarsi of the foot, the first subtalar spacer including a first spacer body portion and a first spacer mount portion, the first spacer body portion including a first articulating surface, a first base surface, and an outer surface extending from the first articulating surface to the first base surface;
   a first fastener coupled to the first spacer mount portion, the first fastener configured to fasten the first subtalar spacer to an inferior surface of a talus bone;
   a second subtalar spacer configured to be implanted in the sinus tarsi of the foot, the second subtalar spacer including a second spacer body portion and a second spacer mount portion, the second spacer body portion including a second articulating surface; and
   a second fastener coupled to the second spacer mount portion, the second fastener configured to fasten the first subtalar spacer to a superior surface of a calcaneus bone, wherein the first subtalar spacer and the second subtalar spacer are collectively shaped to fill a portion of the sinus tarsi and the first articulating surface is configured to articulate with the second articulating surface to direct relative movement between the talus bone and the calcaneus bone of the foot.

16. The apparatus of claim 15, wherein at least a first portion of the first articulating surface is one of convex or concave, and at least a second portion of the second articulating surface is the other of convex or concave to be complementary to the first portion of the first articulating surface.

17. The apparatus of claim 16, wherein the first subtalar spacer and the second subtalar spacer are made of polyethylene.

18. The apparatus of claim 17, wherein the second subtalar spacer is configured to be implanted in the sinus tarsi directly opposite the first subtalar spacer.

19. The apparatus of claim 15, wherein the first subtalar spacer is configured to articulate in one of a sliding, rolling, or rubbing motion with respect to the second subtalar spacer.

20. The apparatus of claim 15, wherein the apparatus is configured to reduce conditions caused by a collapsed sinus tarsi by filling the portion of the sinus tarsi.

* * * * *